(12) United States Patent
Ramaswamy et al.

(10) Patent No.: US 7,546,769 B2
(45) Date of Patent: Jun. 16, 2009

(54) ULTRASONIC INSPECTION SYSTEM AND METHOD

(75) Inventors: Sivaramanivas Ramaswamy, Karnataka (IN); Michael Francis Xavier Gigliotti, Scotia, NY (US); Vamshi Krishna Reddy Kommareddy, Karnataka (IN); Richard Eugene Klaassen, West Chester, OH (US); Edward James Nieters, Burnt Hills, NY (US); Mandayam Tondanur Shyamsunder, Karnataka (IN); Michael Everett Keller, Mason, OH (US); Nihat Kurkcu, Istanbul (TR)

(73) Assignee: General Electric Compnay, Niskayuna, NY (US)

( * ) Notice: Subject to any disclaimer, the term of this patent is extended or adjusted under 35 U.S.C. 154(b) by 439 days.

(21) Appl. No.: 11/291,682

(22) Filed: Dec. 1, 2005

(65) Prior Publication Data

US 2007/0125174 A1 Jun. 7, 2007

(51) Int. Cl.
*G01N 29/00* (2006.01)
(52) U.S. Cl. .............................. 73/579; 73/597; 73/602; 73/628
(58) Field of Classification Search .................. 73/579, 73/645, 1.82, 577, 599, 600, 602, 627, 628, 73/597, 626; 600/441, 443, 447, 458
See application file for complete search history.

(56) References Cited

U.S. PATENT DOCUMENTS

| | | | |
|---|---|---|---|
| 4,265,120 A | | 5/1981 | Morris et al. |
| 4,649,750 A | | 3/1987 | Cantrell, Jr. et al. |
| 4,719,583 A | * | 1/1988 | Takafuji et al. ................ 702/30 |
| 5,475,650 A | * | 12/1995 | Sinha et al. .................... 367/31 |
| 6,132,377 A | | 10/2000 | Bolorforosh et al. |
| 6,197,130 B1 | | 3/2001 | Cantrell et al. |
| 6,226,228 B1 | | 5/2001 | Hossack et al. |
| 6,343,513 B1 | | 2/2002 | Yost et al. |
| 6,401,537 B1 | * | 6/2002 | Gigliotti et al. ................ 73/598 |

(Continued)

FOREIGN PATENT DOCUMENTS

EP 1526379 4/2005

(Continued)

OTHER PUBLICATIONS

J. H. Cantrell et al., "Effective Nonlinearity Parameters of Aluminum Alloys as a Function of Volume Fraction of Second Phase Precipitates," 1986 Ultrasonics Symposium Proceedings; IEEE; pp. 1075-1078.

(Continued)

*Primary Examiner*—Hezron Williams
*Assistant Examiner*—J M Saint Surin
(74) *Attorney, Agent, or Firm*—Penny A. Clarke

(57) ABSTRACT

A method and system for microstructural evaluation and degradation evaluation of an object are provided. The method comprises insonifying at least one subvolume of the object with ultrasonic energy at a fundamental frequency and acquiring receive energy from the object at the fundamental frequency and at least one harmonic frequency thereof. A nonlinearity parameter is determined using the receive energy. The nonlinearity parameter is then used to determine a grain size for the subvolume of the object and a variation of the grain size within the object. The nonlinearity parameter is also used to determine fatigue damage or a residual stress.

28 Claims, 6 Drawing Sheets

U.S. PATENT DOCUMENTS

| | | | |
|---|---|---|---|
| 6,988,410 B2* | 1/2006 | Gilmore et al. | 73/600 |
| 7,056,290 B2* | 6/2006 | Rielly et al. | 600/447 |
| 2002/0009204 A1 | 1/2002 | Matsumura | |
| 2004/0064043 A1 | 4/2004 | Rielly et al. | |
| 2004/0077947 A1 | 4/2004 | Migita | |
| 2005/0087016 A1 | 4/2005 | Gilmore et al. | |

FOREIGN PATENT DOCUMENTS

| | | |
|---|---|---|
| WO | WO98/46139 | 10/1998 |
| WO | 2004-109222 | 12/2004 |

OTHER PUBLICATIONS

J. H. Cantrell, "Residual Strains from Lattice-Generated Stochastic Nonlinear Acoustic Radiation Fields in Solids," 1986 Ultrasonics Symposium Proceedings; IEEE; pp. 1079-1082.

J. H. Cantrell, "Crystalline Structure Dependence of Acoustic Nonlinearity Parameters," 1987 Ultrasonics Symposium Proceedings; IEEE; pp. 425-428.

J. H. Cantrell, "Nonlinear Phenomena in Solid State Physics and Technology," 1990 Ultrasonics Symposium Proceedings; IEEE; pp. 1255-1261.

J. H. Cantrell et al., "Nonlinear ultrasonic characterization of Fatigue Microstructures," International Journal of Fatigue; vol. 23, 2001; pp. 487-490.

D. M. Donskoy et al., "Vibro-Acoustic Modulation Nondestructive Evaluation Technique," Journal of Intelligent Material Systems and Structures, vol. 9; Sep. 1998; pp. 765-771.

J. Frouin et al., "Real-Time Monitoring of Acoustic Linear and Non-linear Behavior of Titanium Alloys During Cyclic Loading," Materials Research Society Symposium—Proceedings, vol. 591; 2000; pp. 79-84.

D. C. Hurley et al., "Experimental Comparison of Ultrasonic Techniques to Determine the Nonlinearity Parameter," 1996 Ultrasonics Symposium Proceedings; IEEE; pp. 495-498.

Young-Chul Jung et al., "Ultrasonic Response to Material Fatigue," Proceedings of the SPIE, vol. 4335, 2001; pp. 180-187.

P. Li et al., "Thermal Strains and Acoustic Nonlinearity in Crystalline Solids," 1984; Ultrasonics Symposium Proceedings; IEEE; pp. 955-957.

P. Li et al., "Dependence of Acoustic Nonlinearity Parameter of Second Phase Precipitates of Aluminum Alloys," 1985; Ultrasonics Symposium Proceedings; IEEE; pp. 1113-1115.

P. B. Nagy, "Fatigue Damage Assessment of Nonlinear Ultasonic Materials Characterization," Ultrasonics; vol. 36; Feb. 1998; pp. 375-381.

W. P. Winfree et al., "Harmonic Generation of Short Ultrasonic Pulses," 1982 Ultrasonics Symposium Proceedings; IEEE; pp. 1026-1028.

H. Yang et al., "Effect of Aging on the Third-Order Elastic Moduli of 18Ni Maraging Steel," 1987 Ultrasonics Symposium Proceedings; IEEE; pp. 1131-1135.

EP Search Report, EP 06125211, Mar. 13, 2007.

K-Y Jhang et al., :Evaluation of material degradation using nonlinear acoustic effect, Ultrasonics, IPC Science and technology Press Ltd., ISSN: 0041-624X, vol. 37, No. 1, Jan. 1999, pp. 39-44.

* cited by examiner

ULTRASONIC INSPECTION SYSTEM AND METHOD

BACKGROUND

The invention relates generally to ultrasonic inspection systems and methods and more specifically to ultrasonic inspection systems and methods for micro-structural evaluation of objects.

Many mechanical failure modes include a long duration first step in which microstructural damage and/or change accumulates in a region, followed thereafter by occurrence of observable cracks and failure. Of the overall service lifetime of a part, only a small amount of life remains once cracks are observable.

Cracks that are above certain threshold sizes, and within certain specified regions, may be detected by existing ultrasound or eddy current techniques. For example, in conventional ultrasonic inspection, ultrasound signals or pulses are transmitted and echo signals are received by a transducer. Discontinuities, such as cracks, can be detected when their echoes are greater than that of the background noise.

Typically, the microstructure of a material in the part determines the various applications in which the parts can be used. Grain size is one important characteristic that is measured to ensure its value lies between a required range, to satisfy the fatigue and creep requirements of the part. It would therefore be desirable to detect regions, which deviate from the specified grain size, as such regions are likely to have undesirable material characteristics. However, when such regions are embedded within the part, detecting the microstructures is a challenge. Also, different product shapes and different processing procedures can produce a variety of grain shapes, which may constrain the ability to measure the grain size.

Accordingly, there is a need to non-destructively detect microstructures of varying sizes, which in turn assists in predicting where a crack might occur in the part.

BRIEF DESCRIPTION

Briefly, in accordance with one aspect of the invention, a method for microstructural evaluation of an object is provided. The method includes insonifying at least one subvolume of the object with ultrasonic energy and acquiring receive energy from the object at a fundamental frequency and at least one harmonic frequency thereof. The method further includes determining a nonlinearity parameter using the receive energy and using the nonlinearity parameter to determine at least one of (a) a grain size for the subvolume of the object and (b) a variation of the grain size within the subvolume of the object.

In another embodiment, an ultrasonic inspection system for micro-structural evaluation of an object is provided. The system includes an ultrasonic transducer configured to insonify at least one subvolume of the object with ultrasonic energy and an ultrasonic receiver configured to acquire receive energy from the object at the fundamental frequency and at least one harmonic frequency thereof. The system further includes a processor configured to determine a nonlinearity parameter using the receive energy. The processor is further configured to use the nonlinearity parameter to determine at least one of (a) a grain size for the subvolume of the object and (b) a variation of the grain size within the object.

In another embodiment, a method for degradation evaluation of an inhomogeneous object is provided. The method comprises insonifying at least one subvolume of the object with ultrasonic energy. The method further includes acquiring receive energy from the object at the fundamental frequency and at least one harmonic frequency thereof and determining a nonlinearity parameter using the receive energy. The method further includes using the nonlinearity parameter to determine at least one of (a) fatigue damage or (b) a residual stress.

In another embodiment, a method for non-destructive evaluation of an object is provided. The method comprises insonifying at least one subvolume of the object with ultrasonic energy and acquiring receive energy from the object at a fundamental frequency and at least one harmonic frequency thereof. The method further includes determining a nonlinearity parameter using the receive energy and using the nonlinearity parameter to determine at least one of an elastic state and a plastic state of the material forming the object.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As used herein, "adapted to," "configured" and the like refer to devices in a system to allow the elements of the system to cooperate to provide a described effect; these terms also refer to operation capabilities of electrical or optical elements such as analog or digital computers or application specific devices (such as an application specific integrated circuit (ASIC)), amplifiers or the like that are programmed to provide an output in response to given input signals, and to mechanical devices for optically or electrically coupling components together.

As used herein, "elastic state of the object" refers to a state of the object in which the atoms deviate from a state of equilibrium. Presence of grains within an object and varying grain sizes in the object contribute to a change in the elastic state of the object. As used herein "plastic state of the object" refers to a state of the object in which a permanent damage occurs to the object. Fatigue and residual stress are examples of contributing factors to a change in the plastic state of the object.

Figure 1:
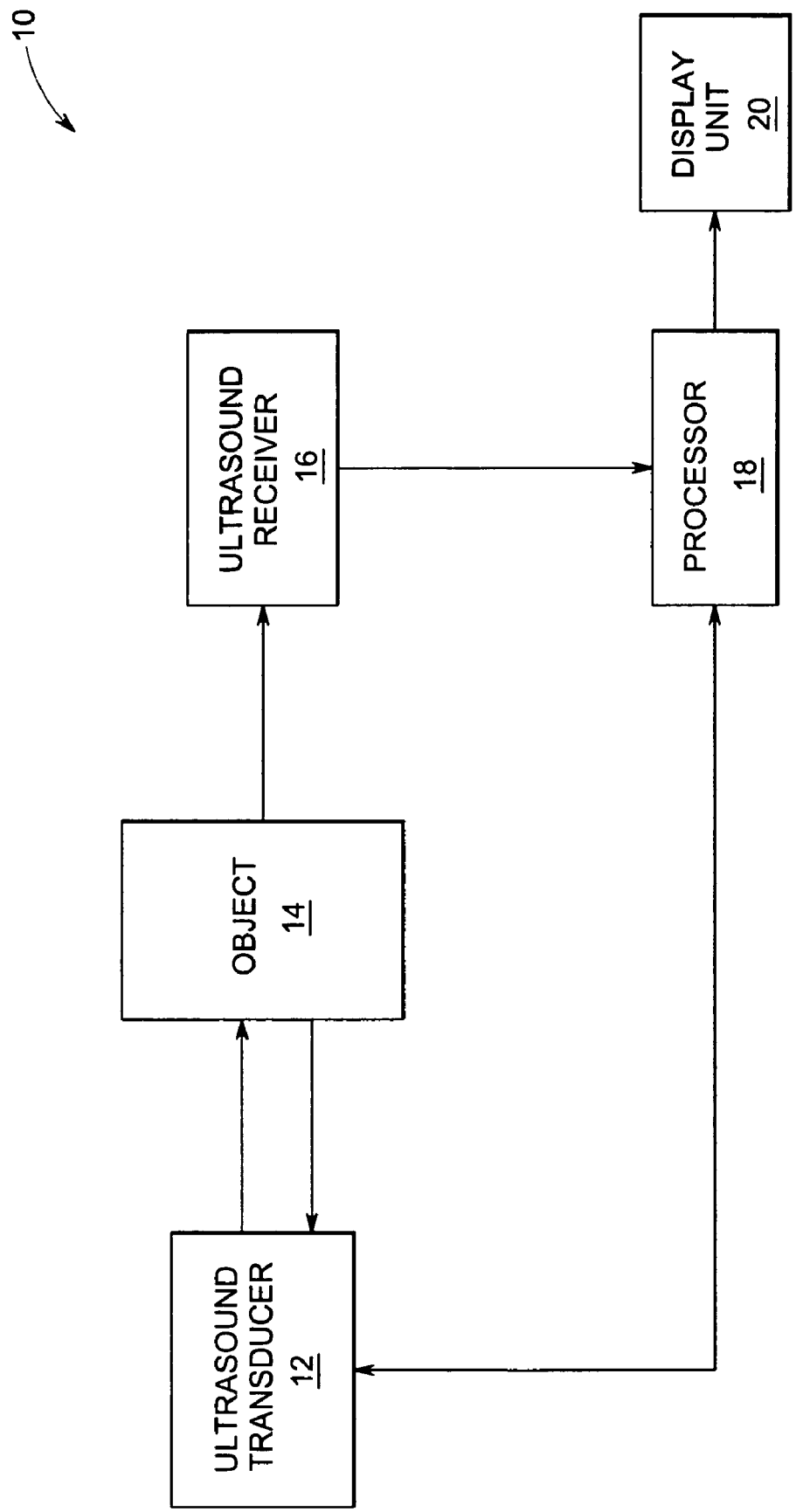
FIG. 1 is a block diagram of an ultrasonic inspection system implemented in accordance with one aspect of the invention.

FIG. 1 is a block diagram of an example through-transmission embodiment of an ultrasonic inspection system used to inspect an object. The system comprises an ultrasonic transducer, an ultrasonic receiver, a processor and optionally, a display unit. Each block is explained in further detail below.

Ultrasonic transducer 12 is configured to transmit ultrasonic energy into at least one subvolume of the object 14. The ultrasonic energy is transmitted at a fundamental frequency $f_0$ in one desired direction into the object 14. In one embodiment, the ultrasound energy is a pure tone signal and is transmitted at a fundamental frequency $f_0$ of 5 MHz. The ultrasonic energy may also be chirp signals, spike pulse signals and combinations thereof. The signal is transmitted repeatedly into the subvolume at various pulser voltage levels. The transducer 12 may take many forms, including a single element probe, a phased array, laser ultrasound and cMUT devices. In one example, the transducer 12 is a broadband transducer having at least a −3 dB bandwidth of $f_0$ and a center frequency of 1.5 $f_0$.

Ultrasonic receiver 16 is configured to acquire energy from the object of at least one harmonic frequency $n*f_0$, where n is an integer, and, optionally, at the fundamental frequency $f_0$. In one embodiment, the ultrasonic receiver is configured to acquire energy at the second harmonic frequency $2 f_0$. In one use of the illustrated example, ultrasonic receiver 16 comprises a transducer (either a single element or array) configured to receive ultrasonic energy from the object 14 at the fundamental frequency and at least one harmonic frequency thereof. In one example, ultrasonic receiver 16 comprises a broadband transducer.

Processor 18 receives the energy data from the ultrasonic receiver and is configured to determine a nonlinearity parameter using the energy data. In addition, processor 18 may be further configured to control transducer 12, as indicated for example in FIG. 1. The nonlinearity parameter is used to determine for example, a grain size for the subvolume of the object and a variation of the grain size within the subvolume of the object. According to a particular embodiment, large grains exhibit a large nonlinearity parameter, and small grains exhibit a small nonlinearity parameter. The nonlinearity parameter can also be used to determine changes in the microstructural characteristics and material properties in the object. In this manner, regions within the object, which deviate from a specified grain size, can be detected. Incipient failure can occur in regions with deviant grain sizes. Beneficially, system 10 can be used to detect such regions regardless of whether they are on the surface of the object or located within the object.

In other embodiments, the nonlinearity parameter is used to determine at least one of fatigue and a residual stress in the object. In other embodiments, the nonlinearity parameter is used to determine at least one of an elastic state and plastic state of the material forming the object.

Figure 2:
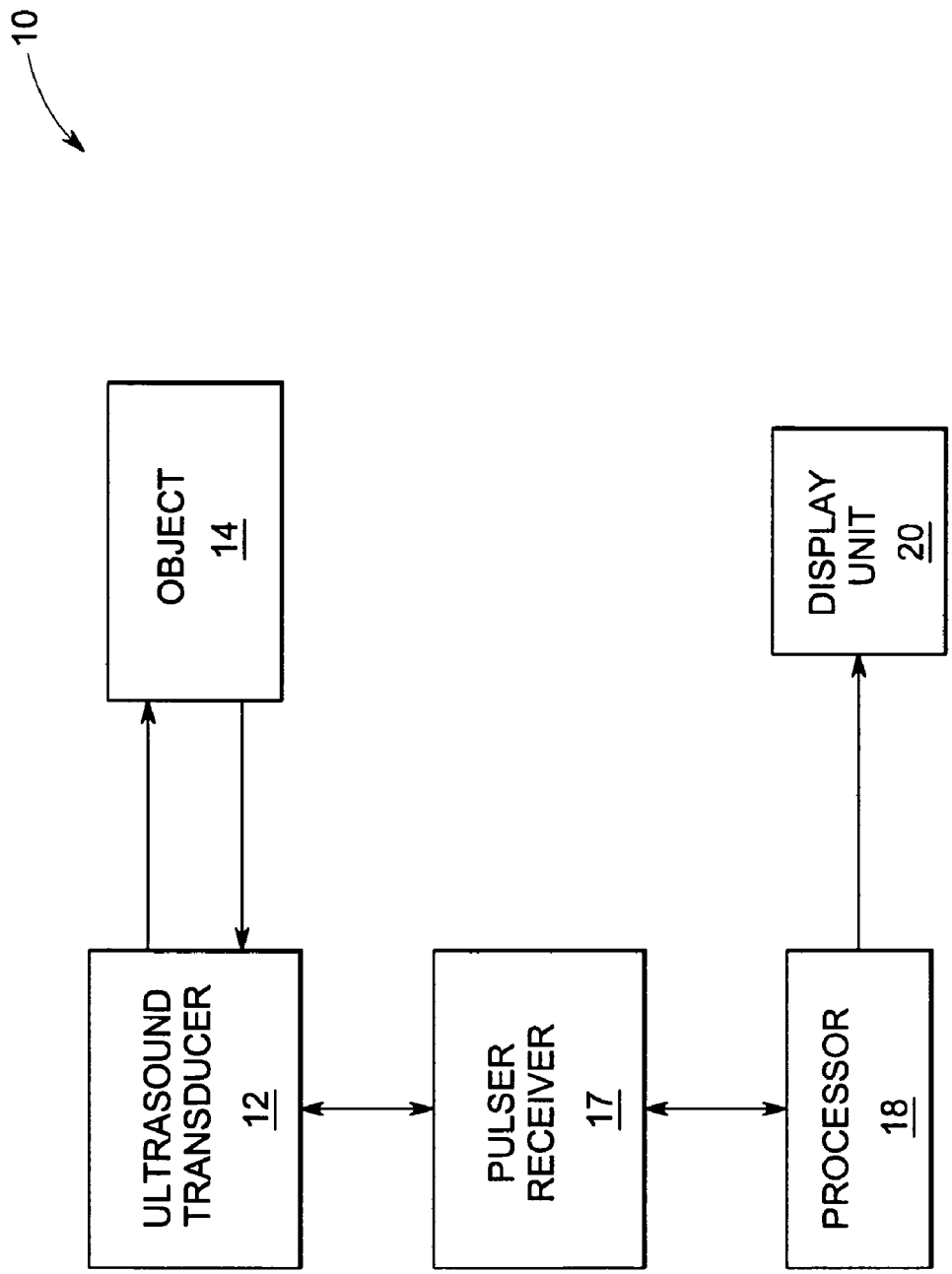
FIG. 2 is a block diagram of an ultrasonic inspection system implemented in accordance with another aspect of the invention.

In one embodiment, the nonlinearity parameter is a function of an amplitude of the second harmonic and of the square of the amplitude of the fundamental frequency. The processor is configured to plot a ratio of the amplitude of the second harmonic to the square of the amplitude of the fundamental frequency FIG. 2 illustrates another exemplary embodiment of system 10. Pulser/receiver 17 is configured to supply excitation signals to transducer 12. The system shown in FIG. 2 is similar to that shown in FIG. 1, except that for the system of FIG. 2, a single transducer 12 is used in a transmit and receive mode to replace the separate transducer and receiver elements of FIG. 1. It therefore should be understood that the transducer and receiver elements can be provided separately or by the same unit, depending on the implementation. Pulser/receiver 17 is configured to supply excitation signals to transducer 12. Upon activation, the transducer 12 transmits ultrasonic energy into at least one subvolume of the object 14. In one embodiment, the ultrasonic energy is transmitted at a fundamental frequency $f_0$. The transducer 12 detects receive energy from the object at the fundamental frequency $f_0$ and at least one harmonic frequency $n*f_0$ thereof, and pulser/receiver 8 receives energy data from the transducer 12. In one embodiment, amplitude data is derived from the receive energy and is representative of the various voltage levels of the transmitted ultrasonic energy. In one example, the transducer comprises a broadband transducer.

Figure 3:
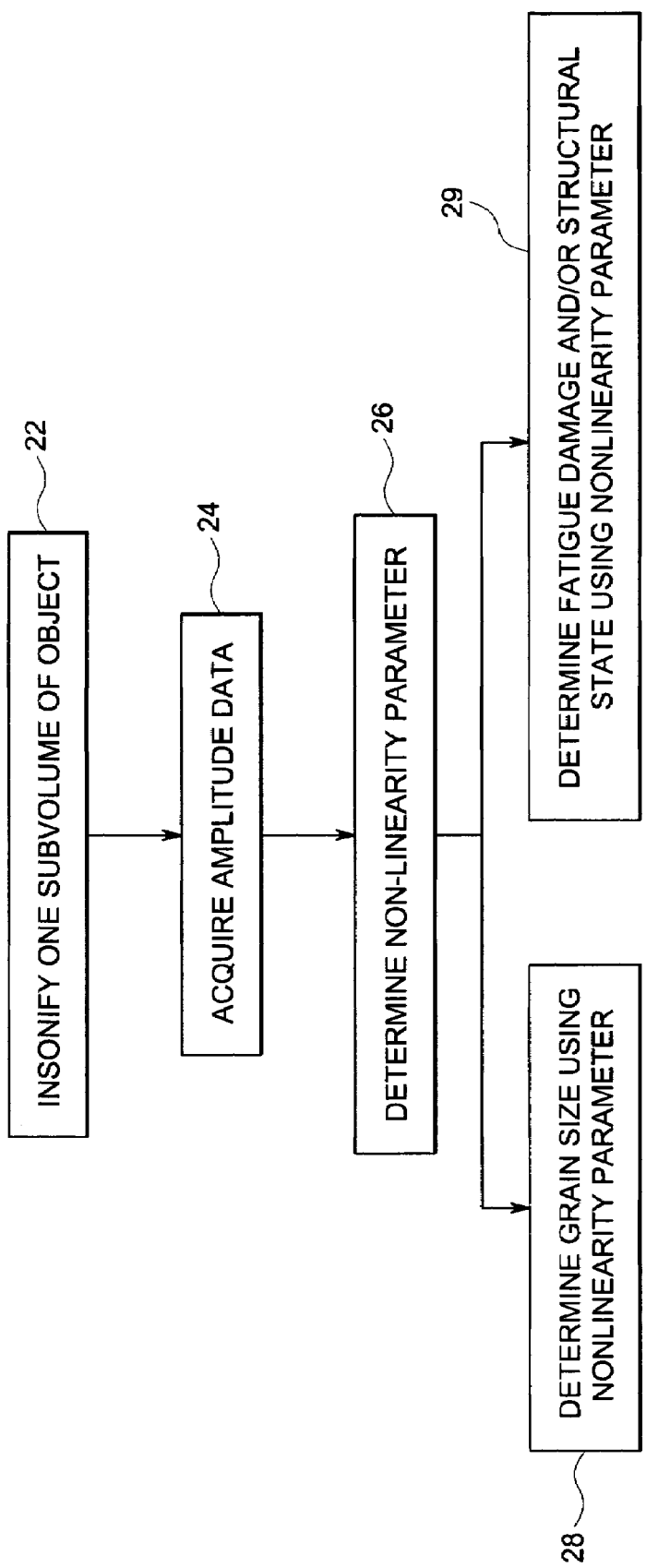
FIG. 3 is a flow chart for one method for microstructural evaluation of an object.

FIG. 3 is a flow chart illustrating one method for microstructural evaluation of an object. In step 22, at least one subvolume of the object is insonified with ultrasonic energy at a fundamental frequency $f_0$. In one example, the fundamental frequency $f_0$ is 5 MHz.

In step 24, energy data from the object is acquired at the fundamental frequency $f_0$ and at least one harmonic frequency $n*f_0$. The energy data is acquired at various amplitude levels for the excitation voltage applied to the transducer 12. In one specific embodiment, the energy data is acquired at the fundamental frequency $f_0$ and the second harmonic frequency $2 f_0$.

In step 26, a nonlinearity parameter is determined using the signal amplitude data derived from the received energy. The nonlinearity parameter is a function of the amplitude of the second harmonic $2 f_0$ and of the square of the amplitude of the fundamental frequency $f_0$. In a further embodiment, a ratio of the amplitude of the second harmonic $2 f_0$ and the square of the amplitude of the fundamental frequency $f_0$ is plotted to obtain the nonlinearity parameter.

Figure 4:
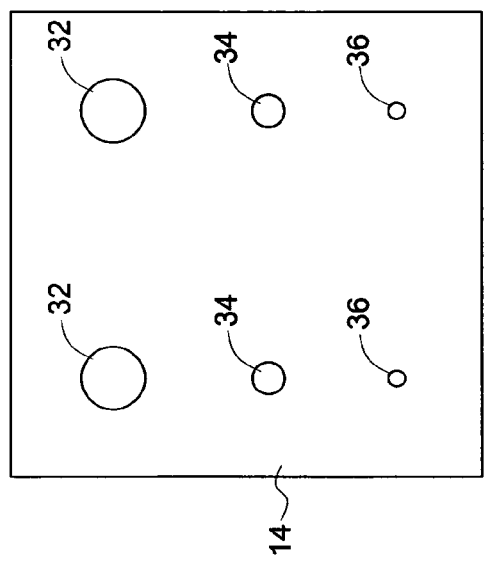
FIG. 4 is a top view of an object being inspected using an ultrasonic inspection system.
Figure 5:
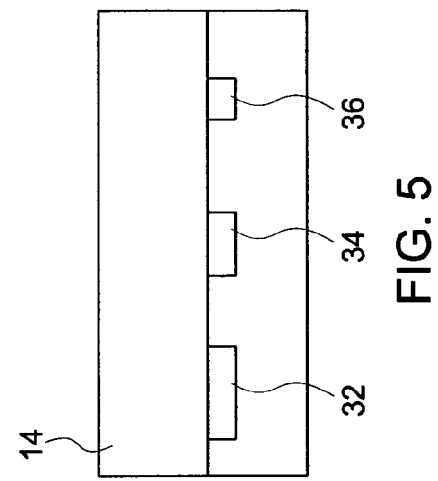
FIG. 5 is a side view of an object being inspected using an ultrasonic inspection system.

FIG. 4 is a block diagram of a sample object being inspected by the ultrasonic system described above. For this example, the sample object 14 comprises fine grain Titanium. The object also includes large grain regions 32, 34 and 36 embedded within the object. The sizes of the large grain regions 32, 34 and 36 are varying as can been seen in the FIG. 4. FIG. 5 is a side view of the object 14. The large grain regions are embedded at approximately 13 mm from the top surface of the object. In one embodiment, the large grain regions are formed of the same material as the object.

Figure 6:
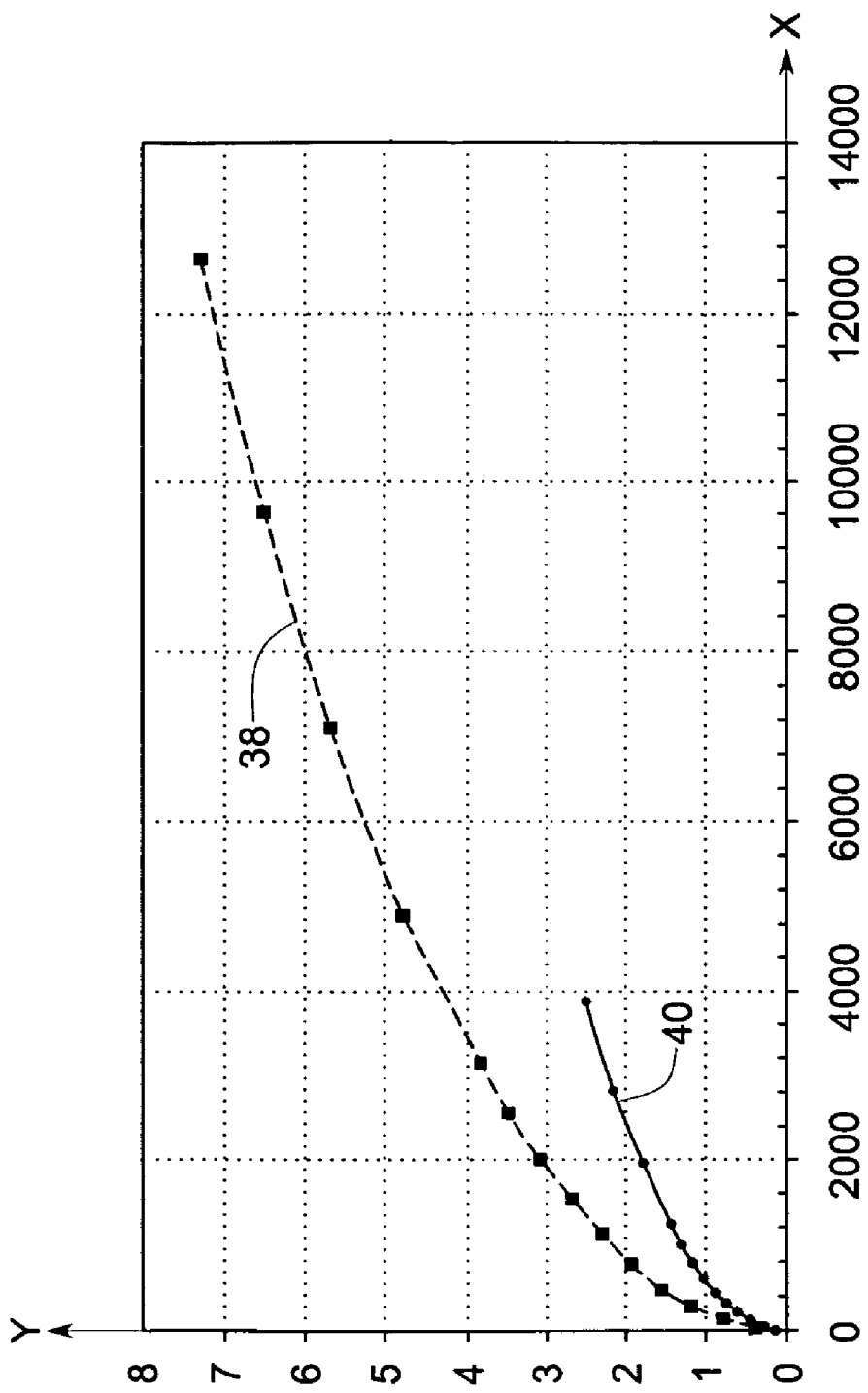
FIG. 6 is a graph illustrating plots of two nonlinearity parameters determined using one aspect of the invention.

FIG. 6 is a graph illustrating a plot of two nonlinearity parameters determined using the technique described in FIG. 3. The y-axis represents the second harmonic frequency $2 f_0$ amplitude and the x-axis represents the square of the amplitude of the fundamental frequency $f_0$. As the probe moves from a region with fine grains to a region comprising large grains, the nonlinearity parameter is altered. The plot that is obtained when the probe is moving over the region with fine grains is represented by reference numeral 38. Similarly, the plot that is obtained when the probe is moving over the region with large grains is represented by reference numeral 40.

In one embodiment, a value of the nonlinearity parameter is a function of the grain size for the subvolume of the object. From that function, an equation may be generated that relates measured nonlinearity parameter to grain size. In a further embodiment, the grain size is determined by measuring the nonlinearity parameter and applying the equation described above. A threshold for the nonlinearity value may be established beyond which the material grain sizes are unacceptable. The threshold value may be user defined or may be determined using at least one calibration sample.

Continuing with FIG. 3, in step 28, the nonlinearity parameter is used to determine a grain size for the subvolume of the object. The nonlinearity parameter may also be used to measure a variation of the grain size within an object. In one embodiment, the nonlinearity parameter 'β' is determined using the following equation:

$$\beta = \frac{8}{ak^2} \frac{(a_2)}{(a_1)^2} \qquad \text{Equation (1)}$$

where 'a' is a distance propagated by the ultrasound energy, k is the propagation vector; $a_1$ is the amplitude of the signal at the fundamental frequency $f_0$, and $a_2$ is the amplitude of the signal at the second harmonic frequency $f_2$. The variation in grain size can be estimated from the variations in 'β' measured in selected subvolumes.

Figure 7:
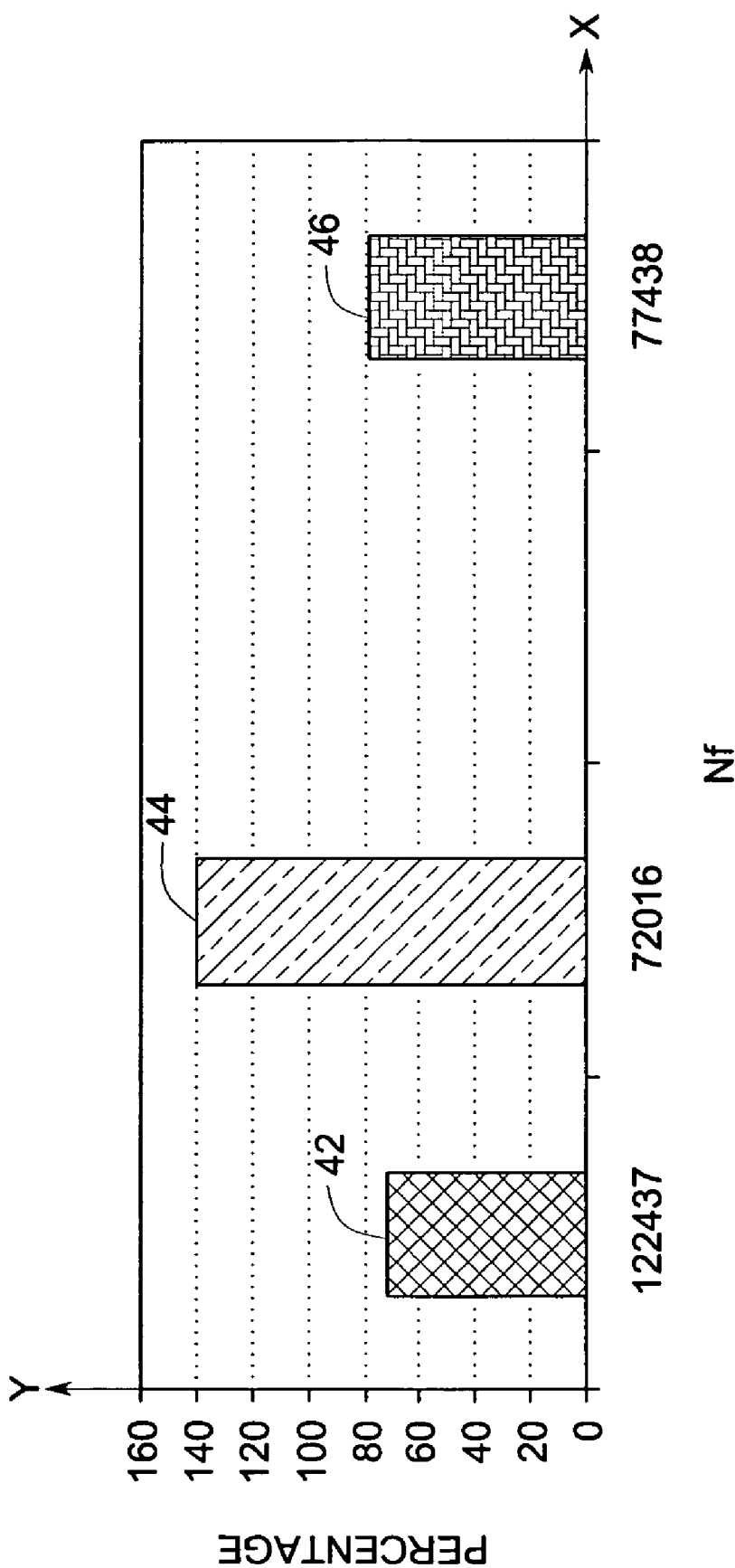
FIG. 7 is a graph illustrating one manner in which low cycle fatigue damage is displayed.

In step 29, the nonlinearity parameter is used to determine a fatigue damage and/or structural state of an inhomogeneous object. As used herein, inhomogeneous object refers to the structural state of the object when it is described by a strain gradient across the material of the volume. The nonlinearity parameter is measured in volumes where no damage or service exposure could have occurred and this nonlinearity parameter is compared to that measured in volumes suspected to have damage. The relative difference in 'β' is used as a measure of degree of damage. FIG. 7 is a graph illustrating one manner in which low cycle fatigue damage is displayed. The x-axis represents 'number of cycles to failure' and the y-axis represents the percentage difference in the nonlinearity parameter between undamaged and damaged objects. Reference numerals 42 and 44 represent a sample object comprising Titanium and reference numeral 46 represents a sample object comprising a nickel based superalloy.

The above described invention has several advantages including the ability to detect material changes within an object in a nondestructive manner. The technique also reduces the time required to perform the test. As the system employs nondestructive testing techniques, the costs for conducting the test are also reduced. The nondestructive testing also ensures an extended life of the object being tested.

Although only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for microstructural evaluation of an object, said method comprising:
   insonifying at least one subvolume of the object with ultrasonic energy;
   acquiring receive energy from the object at the fundamental frequency and at least one harmonic frequency thereof;
   determining a nonlinearity parameter using the receive energy; and
   using the nonlinearity parameter to determine at least one of (a) a grain size for the subvolume of the object and (b) a variation of the grain size within the object.

2. The method of claim 1, wherein the using step comprises:
   generating an equation that relates the nonlinearity parameter to the grain size; and
   applying the equation to the determined nonlinearity parameter to determine the grain size for the subvolume of the object.

3. The method of claim 2, wherein the acquiring step comprises acquiring amplitude data at the second harmonic frequency.

4. The method of claim 3, wherein the nonlinearity parameter is a function of an amplitude of the second harmonic and of the square of the amplitude of the fundamental frequency.

5. The method of claim 2, wherein the using step comprises comparing the nonlinearity parameter to at least one threshold value.

6. The method of claim 5, further comprising determining the threshold value using at least one calibration sample.

7. The method of claim 5, wherein the threshold value is user specified.

8. The method of claim 2, wherein the using step further comprises using at least one calibration sample.

9. The method of claim 1, wherein the using step comprises using the nonlinearity parameter to determine the variation of the grain size within the object.

10. The method of claim 1, wherein the acquiring step comprises acquiring amplitude data at the second harmonic frequency, wherein the nonlinearity parameter is a function of an amplitude of the second harmonic and of the square of the amplitude of the fundamental frequency, and wherein the using step further comprises plotting a ratio of the amplitude of the second harmonic as the square of the amplitude of the fundamental frequency.

11. The method of claim 1, wherein a value of the nonlinearity parameter is proportional to the grain size for the subvolume of the object and the variation of grain size within the object.

12. The method of claim 1, wherein the insonifying comprises insonifying the subvolume at a plurality of pulser voltages, and wherein the acquiring step comprises acquiring amplitude data for the pulser voltages.

13. The method of claim 1, wherein the insonifying comprises applying at least one of a plurality of toneburst signals, chirp signals, spike pulse signals and combinations thereof.

14. An ultrasonic inspection system for microstructural evaluation of an object, said system comprising:
   an ultrasonic transducer configured to insonify at least one subvolume of the object with ultrasonic energy;
   an ultrasonic receiver configured to acquire receive energy from the object at the fundamental frequency and at least one harmonic frequency thereof; and
   a processor configured to determine a nonlinearity parameter using the receive energy, wherein the processor is further configured to use the nonlinearity parameter to determine at least one of (a) a grain size for the subvolume of the object and (b) a variation of the grain size within the object.

15. The system of claim 14, wherein the processor is further configured to:
   generate an equation that relates the nonlinearity parameter to the grain size; and
   apply the equation to the determined nonlinearity parameter to determine the grain size for the subvolume of the object.

16. The system of claim 15, wherein the ultrasonic receiver is further configured to acquire amplitude data at the second harmonic frequency.

17. The system of claim 16, wherein the nonlinearity parameter is a function of an amplitude of the second harmonic and of the square of the amplitude of the fundamental frequency.

18. The system of claim 14, wherein the processor is further configured to use the nonlinearity parameter to determine the variation of the grain size within the object.

19. The system of claim 14, wherein the ultrasonic receiver is further configured to acquire amplitude data at the second harmonic frequency, and wherein the processor is further configured to plot a ratio of the amplitude of the second harmonic to the square of the amplitude of the fundamental frequency.

20. The system of claim 14, wherein the ultrasonic transducer is configured to insonify the subvolume at a plurality of pulser voltages, and wherein the ultrasonic receiver is configured to acquire amplitude data for the pulser voltages.

21. A method for degradation evaluation of an object, said method comprising:
  insonifying at least one subvolume of the object with ultrasonic energy, wherein the object is inhomogeneous;
  acquiring receive energy from the object at the fundamental frequency and at least one harmonic frequency thereof;
  determining a nonlinearity parameter using the receive energy; and
  using the nonlinearity parameter to determine a plurality of gradients in a residual stress.

22. A method for nondestructive evaluation of an object, said method comprising:
  insonifying at least one subvolume of the object with ultrasonic energy;
  acquiring receive energy from the object at a fundamental frequency and at least one harmonic frequency thereof;
  determining a nonlinearity parameter using the receive energy; and
  using the nonlinearity parameter to determine at least one of an elastic state and a plastic state of the material.

23. The method of claim 22, wherein the using step comprises using the nonlinearity parameter to determine the grain size for the subvolume of the object.

24. The method of claim 22, wherein the using step comprises using the nonlinearity parameter to determine the variation of the grain size within the object.

25. The method of claim 22, wherein the using step comprises using the nonlinearity parameter to determine fatigue damage in the object.

26. The method of claim 22, wherein the using step comprises using the nonlinearity parameter to determine a residual stress.

27. The method of claim 22, wherein the acquiring step comprises acquiring amplitude data at the second harmonic frequency.

28. The method of claim 22, wherein the nonlinearity parameter is a function of an amplitude of the second harmonic and of the square of the amplitude of the fundamental frequency.

* * * * *

UNITED STATES PATENT AND TRADEMARK OFFICE
CERTIFICATE OF CORRECTION

PATENT NO. : 7,546,769 B2  Page 1 of 1
APPLICATION NO. : 11/291682
DATED : June 16, 2009
INVENTOR(S) : Ramaswamy et al.

It is certified that error appears in the above-identified patent and that said Letters Patent is hereby corrected as shown below:

On the Face Page, in Field (73), under "Assignee", in Column 1, Line 1, delete "Compnay," and insert -- Company, --, therefor.

On Page 2, in Field (56), under "OTHER PUBLICATIONS", in Column 2, Line 16, delete "Ultasonic" and insert -- Ultrasonic --, therefor.

Signed and Sealed this

Tenth Day of November, 2009

David J. Kappos
*Director of the United States Patent and Trademark Office*